United States Patent
Ferek-Petric

[11] Patent Number: 5,693,074
[45] Date of Patent: Dec. 2, 1997

[54] CARDIAC ELECTROTHERAPY DEVICE FOR CARDIAC CONTRACTION MEASUREMENT

[75] Inventor: Bozidar Ferek-Petric, Zagreb, Croatia

[73] Assignee: Pacesetter AB, Solna, Sweden

[21] Appl. No.: 652,512

[22] PCT Filed: Dec. 5, 1994

[86] PCT No.: PCT/EP94/04041

§ 371 Date: Jun. 4, 1996

§ 102(e) Date: Jun. 4, 1996

[87] PCT Pub. No.: WO95/15784

PCT Pub. Date: Jun. 15, 1995

[30] Foreign Application Priority Data

Dec. 6, 1993 [HR] Croatia ................... P931478A

[51] Int. Cl.$^6$ ........................... A61N 1/362
[52] U.S. Cl. ........................... 607/9; 128/642
[58] Field of Search ........................... 607/6, 9, 17, 20, 607/24, 119, 122, 154–156; 128/642

[56] References Cited

U.S. PATENT DOCUMENTS

| | | |
|---|---|---|
| 3,815,611 | 6/1974 | Denniston, III . |
| 3,942,534 | 3/1976 | Allen et al. . |
| 4,291,707 | 9/1981 | Heilman et al. . |
| 4,475,551 | 10/1984 | Langer et al. . |
| 4,535,774 | 8/1985 | Olson . |
| 4,572,191 | 2/1986 | Mirowski et al. . |
| 4,600,017 | 7/1986 | Schroeppel . |
| 4,614,192 | 9/1986 | Imran et al. . |
| 4,662,377 | 5/1987 | Heilman et al. . |
| 4,686,987 | 8/1987 | Salo et al. . |
| 4,766,902 | 8/1988 | Schroeppel . |
| 4,768,511 | 9/1988 | DeCote, Jr. . |
| 4,768,512 | 9/1988 | Imran . |
| 4,774,950 | 10/1988 | Cohen . |
| 4,779,617 | 10/1988 | Whigham . |
| 4,790,317 | 12/1988 | Davies . |
| 5,201,808 | 4/1993 | Steinhaus et al. ............... 607/20 |
| 5,243,976 | 9/1993 | Ferek-Petric et al. ............ 607/6 |
| 5,261,418 | 11/1993 | Ferek-Petric . |
| 5,271,292 | 12/1993 | Ferek-Petric . |
| 5,361,776 | 11/1994 | Samuelson et al. ............... 607/9 |
| 5,514,171 | 5/1996 | Hoegnelid et al. ............... 607/122 |

FOREIGN PATENT DOCUMENTS

WO/8809684  12/1988  WIPO .

*Primary Examiner*—William E. Kamm
*Assistant Examiner*—George R. Evanisko
*Attorney, Agent, or Firm*—Hill, Steadman & Simpson

[57] ABSTRACT

A cardiac electrotherapy device comprises an elongated elastic lead body having a distal electrode adapted to be connected to the heart; lead body including a sensor portion at a location adapted to undergo deformations responsive to heart muscles contractions when the lead body is connected to the heart. The lead body forms a high frequency transmission line, having two conductors which are provided with terminals at the proximal end of the lead and which are adapted to transmit high frequency signals from the terminals to the sensor portion of the lead and vice versa. The sensor portion varies its high frequency electric parameters when being subjected to said deformations.

26 Claims, 7 Drawing Sheets

60 ABSOLUTE VALUE
61 PHASE

FIG. 7

CARDIAC ELECTROTHERAPY DEVICE FOR CARDIAC CONTRACTION MEASUREMENT

FIELD OF THE INVENTION

This invention relates to cardiac pacemakers and implantable cardioverters—defibrillators, more particularly to improved detection of pathologic tachycardias and fibrillation, as well as to more physiologic sensor for rate responsive pacing and accurate detection of pacing capture.

BACKGROUND AND PRIOR ART

Tachycardia is a condition in which the heart beats rapidly. Pathologic tachycardia is the one which disturbs the hemodynamics, causing the drop of systemic blood pressure. There are many types of pathologic tachycardias and the electrophysiology differentiates two major classes: supraventricular and ventricular tachycardias. Tachycardia is often the result of electrical feedback within the heart structures where the natural beat results in the feedback of an electrical stimulus which prematurely triggers another beat. There are several different cardiac pacing modes which may terminate the tachycardia. The underlying principle in all of them is that if a pacemaker stimulates the heart at least once shortly after a heartbeat, before the next naturally occurring heartbeat at the rapid rate, the interposed stimulated heartbeat disrupts the stability of the feedback loop thus reverting the tachycardia to sinus rhythm. Such a pacemaker was disclosed in the U.S. Pat. No. 3,942,534 which, following detection of tachycardia, generates a stimulus after a delay interval. The most hazardous arrhythmia is ventricular tachycardia which may progress in the lethal arrhythmia ventricular fibrillation. Because the ventricular tachycardia is not always successfully treated and terminated by antitachycardia pacing, the implantable cardioverter—defibrillator is used to deliver the high energy pulse shock in order to cause the cardioversion of ventricular tachycardia to sinus rhythm. Such an implantable device was disclosed in the U.S. Pat. No. 4,614,192 comprising a bipolar electrode for R-wave sensing, the system utilizing heart rate averaging and probability density function for fibrillation detection. The similar system for cardioversion is disclosed in the U.S. Pat. No. 4,768,512 which has the high frequency pulse delivery. All these systems deliver high energy shock through the special patch-electrodes such as described in the U.S. Pat. No. 4,291,707. In order to simplify the surgical procedure, systems comprising superior vena cava electrode and subcutaneous electrode, such as described in the U.S. Pat. No. 4,662,377, have been developed. The supraventricular tachycardia caused by atrial flutter or fibrillation can be also treated by implantable cardioverter such as described in the U.S. Pat. No. 4,572,191. The difficulty in the electrotherapy treatment of tachycardia is that the implantable apparatus has to comprise means for the accurate detection of pathologic tachycardia in order to deliver the electrotherapy pulses whenever the pathologic tachycardia occurs. The problem is that the heart rhythm increases its frequency physiologically whenever either the physical or the emotional stress occurs. The means for pathologic tachycardia detection must accurately differentiate the natural sinus tachycardia which may not be treated by means of electrotherapy from the pathologic tachycardia which has to be treated. Therefore the discrimination between normal and pathologic tachycardia on the basis of frequency measurement is not reliable. In order to overcome this problem numerous methods of tachycardia detection have been developed which are applicable in the implantable electrotherapy devices.

Such a system has been disclosed in the U.S. Pat. No. 4,475,551 where the heart rate sensing as well as probability density function were used to distinguish between ventricular fibrillation and high rate tachycardia. More sophisticated system has been disclosed in the U.S. Pat. No. 4,790,317 which can automatically recognize the pathologic rhythm by means of monitoring of the pulse sequence representing the ventricular electrical activity. At least two sensing positions i.e. to each ventricular epicardial surface are used, but more sensing points will obtain better discrimination between normal and pathologic rhythms.

The problems which may occur with such systems are susceptibility on electromagnetic interference and muscular noise, as well as improper gain of the heart beat detectors causing the undersensing of cardiac rhythm. Therefore some means for detecting of noise and for automatic sensitivity adjustment is desirable.

Therefore the implanted pacemaker noise rejection system described in the U.S. Pat. No. 4,779,617, as well as the automatic sensitivity control systems disclosed in the U.S. Pat. No. 4,766,902 and U.S. Pat. No. 4,768,511 have been developed. The implantable cardioverting system usually comprises the cardiac pacing system because of the backup of bradycardial events which follow the cardioversion high voltage pulse. There are also patients who suffer from pathologic tachycardia as well as from bradycardia which has to be treated by cardiac pacing. Therefore the physiological sensor for control of the heart rate is desirable in order to obtain the rate responsive pacing. It is also possible that the cardioversion implantable device comprises a dual chamber physiologic pacing function. In such a system a sensor for atrial fibrillation detection would be important not only for the appropriate ventricular response on atrial rhythms, but also for differentiating supraventricular from ventricular tachycardia. There are many physiological control systems for rate responsive pacing, but only few of them can be used for tachycardia detection as well. As far as it is known to the inventor, none of these sensor systems can be used for ventricular tachycardia detection, rate responsive pacing, for atrial fibrillation detection, for pacing capture confirmation and for noise detection. The system disclosed in the U.S. Pat. No. 4,774,950 comprises a circulatory systemic blood pressure measurement system which detects the drop of pressure in the case of pathologic heart rhythm.

Furthermore the stroke volume and ventricular volume measurement is possible in the system described in the U.S. Pat. No. 4,686,987 as well as in the U.S. Pat. No. 4,535,774.

U.S. Pat. No. 3,815,611 discloses the measurement of the lead tip flexions by means of the variable impedance flexible resistor for only the lead tip flexions detection. Variable resistor is therefore mounted fixed at the lead tip. Such disclosure is convenient for measurement of local bending detection of the lead tip caused by the apical muscle contraction precisely the septum. Actually, in chronic phase when fibrous channel encloses the lead, the transducer, such as disclosed in relevant document, moves together with ventricular septum having the same magnitude of movements. In the invention of this application, the magnitude of movements of transmission line depends on the lead body resistance to the forces of the entire ventricle which bend the lead in the region being distant from the apical region (transatrial curvature).

U.S. Pat. No. 4,600,017 discloses system dedicated to the pressure measurements, design being a compromise between the obligatory electrical insulation from the blood and the fact that the silicone covering the sensor decreases the sensitivity of the sensor. A normally insulated pacing lead comprises the transducer adjacent to the lead body outer wall surface.

Obviously all these systems measure indirectly the mechanical contraction of the heart that is the consequence of the electrical depolarization and which has the performance influenced by sympathetic and parasympathetic nervous system as well as by circulatory cathecholamines. Sympathetic stimulation as well as elevation of the circulatory cathecholamines concentration increase the velocity of the contraction and therefore the hemodynamic forces are accordingly transferred to the circulatory system. The contraction acceleration is therefore a ventricular inotropic parameter modified during exercise. The quality of the mechanical cardiac contraction significantly differs in normal and pathologic rhythms. Therefore the system for direct measurement of parameters of the mechanical cardiac contraction, as it is disclosed in the present invention, obtains more exact physiological parameters which may be used for closed loop rate responsive pacing regulation, as well as for different cardiac rhythm detection. In contrary to the previously described systems, in disclosed system of this patent application, the cardiac contraction energy is transformed directly into the mechanical stretching energy within the lead body thereby producing the high frequency signal parameters variation within the lead body which is mechanically coupled to the heart muscle. Therefore, cardiac contraction provides the high frequency signal variations having amplitude and frequency characteristics representing the same characteristics of the contraction itself, consequently enabling the high frequency signal processing in such a way as to obtain the information about the contraction amplitude and velocity being sensors for cardiac electrotherapy control. There is no external mechanical energy which can impede the lead tension measurement signal, as well as there is no significant influence of the fibrotic tissue to the signal.

My U.S. Pat. No. 5,261,418 and my U.S. Pat. No. 5,271,392 disclose a system for lead tension measurement comprising so-called tensiometric transducers. These transducers may be produced of either the piezoelectric material or the conductive rubber. Both materials may be used for production of tensiometric stylets. In these patent applications, there is a possibility to use a standard pacing lead for tensiometric measurement. Normally, the stylet channel of a lead enables the control of the lead implantation by means of a steel wire (stylet) insertion. Manipulating the stylet i.e. rotating, pushing and pulling governs the direction of the lead tip. After the proper positioning of the lead tip, the stylet is pulled-out. Therefore every implanted lead comprises an empty stylet channel which may be used for the permanent insertion of a stylet which may be used for lead tension measurement. In contrary to these applications, the present invention discloses a system without a special transducer, wherein the stylet channel is used for insertion of an electric conductor which constitutes a high frequency transmission line together with a lead conductor. European Pat. No. 461-539 as well as U.S. Pat. No. 4,291,707 specify tensiometric patch, but there is no disclosure of defibrillator patch comprising a transmission line.

WO-A-88/09684 discloses a sensing system for detecting the frequency and amplitude of motion of a patient's diaphragm comprising a transducer, a cardiac lead coupled to the transducer and a sensing instrument coupled to the lead for correlating transducer movement with the frequency and amplitude of diaphragm motion. The transducer can include a pair of capacitance plates having a gap between the plates that varies in proportion to the diaphragm motion or a pulsed photoelectric signal generator and photoelectric signal receiver adapted for sensing an optical signal transmitted by the generator.

U.S. Pat. No. 5,109,842 discloses a motion sensor which may be mounted onto the restricted and relatively small area of a defibrillator patch. Motion sensor such as disclosed in this patent detects mechanical cardiac motion in only one restricted area having contact with myocardium. Relevant patent discloses the system which produces the signal during the cardiac motion at the region of epicardium whereon the transducer is fixed.

SUMMARY OF THE INVENTION

It is an object of this invention to provide a cardiac electrotherapy device which is able to measure the heart muscles contractions directly and with high precision.

The invention is characterized by the features of claim 1. Advantageous embodiments of the invention are subject of the remaining claims.

The term "high frequency" used in this application covers frequencies in an area of about 5 MHz to 100 MHz.

According to the present invention, the system for lead tension measurement is incorporated within the implantable electrotherapy apparatus in order to achieve the measurement of the mechanical contractions of the heart muscle. The measurement system comprises specially designed lead being a high frequency transmission line. In another embodiment, the measurement system comprises the insulated styler within the cardiac pacing lead, wherein the lead conductor and the stylet form a coaxial cable being a high frequency transmission line. The transmission line is mechanically coupled to the heart muscle, wherein mechanical stress to the lead produces variation of the electrical parameters of the transmission line. The implantable electrotherapy apparatus comprises electronic circuits for either analyzing or measuring the high frequency signal transmission and reflection variations produced within the aforementioned transmission line and caused by means of the cardiac muscle contractions. It can transmit a high frequency signal to the transmission line and to continously monitor the characteristic impedance and voltage standing wave ratio at the input of the transmission line. Signal processing of the high frequency signal provides cardiac contraction detection, pathologic tachycardia recognition and ventricular inotropic parameter used for rate responsive pacing regulation.

There are several principles of measurements of the transmission line parameters:

1. A kind of measurement bridge (for instance Schering bridge) measuring the line impedance, using the high-frequency sinusoidal signal (between 5 and 100 MHz).

2. Reflection coefficient measurement by means of the directional coupler again by the high-frequency sinusoidal signal (between 5 and 100 MHz).

3. Standing waves ratio measurement

4. Pulse reflectometry—whereby the narrow single pulse is emitted and the time interval between emission and its reflection is measured. The narrow single pulse has a very broad frequency spectrum dependent on its duration and repetition rate.

A cardiac electrotherapy system according to the invention comprises a cardiac lead being a transmission line means; a high frequency electronic circuitry means for electric parameters measurement of the said transmission line, and for processing of the said electric parameters, said parameters varying due to the bending of said cardiac pacing lead, said bending being caused by the heart muscle contractions; cardiac pacing means for providing pacing signal to the heart; and control means responsive to the measured parameters of said transmission line for controlling the pacing signals to the heart.

In a first embodiment of the invention said cardiac lead has a distal electrode adapted to be connected to the heart and comprises an elastic, plastic body; an electrical conductor contained within said plastic body having an interior stylet channel, terminating in an electrode for delivery of pacing pulses; an insulated styler wire disposed in said stylet channel at a location at which bending distortions of said plastic body occur due to said heart muscle contractions when said plastic body is implanted in said heart or attached to said heart, said insulated stylet wire and said electrical conductor forming a transmission line which changes its electrical parameters dependent on the frequency and magnitude of said heart muscle contractions.

In a second embodiment of the invention said cardiac lead has a distal electrode adapted to be connected to the heart and comprises: an elastic, plastic body; a first electrical conductor contained within said plastic body terminating in an electrode for delivery of pacing pulses; a second electrical conductor at a location at which bending distortions of said plastic body occur due to said heart muscle contractions when said plastic body is implanted in said heart or attached to said heart, said second electrical conductor and said first electrical conductor forming a transmission line which changes its electrical parameters, especially its capacitance dependent on the frequency and magnitude of said heart muscle contractions.

Said high frequency electronic circuitry means for electric parameters measurement of the said transmission line provides a signal representing the variation of said parameters caused by variation of the geometry of said transmission line, said signal being generated by the said heart muscle contractions and said signal's amplitude and frequency characteristics representing amplitude and frequency characteristics of said heart muscle contractions.

Said signal may be a representation of the variation of the sending end vector impedance or of the voltage standing wave ratio or of the reflection coefficient of said transmission line.

Said high frequency electronic circuitry means for electric parameters measurement of the said transmission line may comprise a high frequency bridge means, e.g. a Schering bridge, said bridge means being balanced when no force or an initial force, caused by the specific implantation position is applied to said lead, and said bridge being unbalanced whenever a force is applied to said lead.

Said control means responsive to the measured parameters of said transmission line for controlling the pacing signals to the heart preferably includes means for cardiac arrhythmia detection and differentiation between various arrhythmias or means includes means for the pacing rate modulation in rate responsive pacing mode or means for pacing capture confirmation.

In another embodiment of the invention said high frequency electronic circuitry for electric parameters measurement of the said transmission line comprises means for matching the output impedance of said circuitry to the input impedance of said transmission line.

To this end said lead may comprise a connector means on its proximal end, said connector providing electrical connection between said transmission line and said high frequency electronic circuitry, without impeding said matching of said impedances.

In case of the first embodiment, mentioned above said electrical conductor may be connected to the first pole of said high frequency electronic circuitry, and said stylet wire is connected to the second pole of said high frequency electronic circuitry.

In case of the second embodiment, mentioned above said first electrical conductor may be connected to the first pole of said high frequency electronic circuitry, and said second electrical conductor may be connected to the second pole of said high frequency electronic circuitry.

Preferably said transmission line comprises termination means at its distal end. Said termination may be an open circuit, a short circuit or may have an impedance matched to the impedance of said transmission line.

In a cardiac electrotherapy system wherein said termination means varies its impedance because of the said lead body tension being caused by the heart muscle contractions, said impedance variation generates a mismatching of said termination to said transmission line, whereby frequency and extent of said mismatching depend on frequency and magnitude of said heart muscle contractions and can be used for electric parameters measurement of the said transmission line.

DESCRIPTION OF THE DRAWINGS

FIG. 8 is a cross-section of a defibrillator patch.

DESCRIPTION OF THE PREFERRED EMBODIMENT

Figure 1:
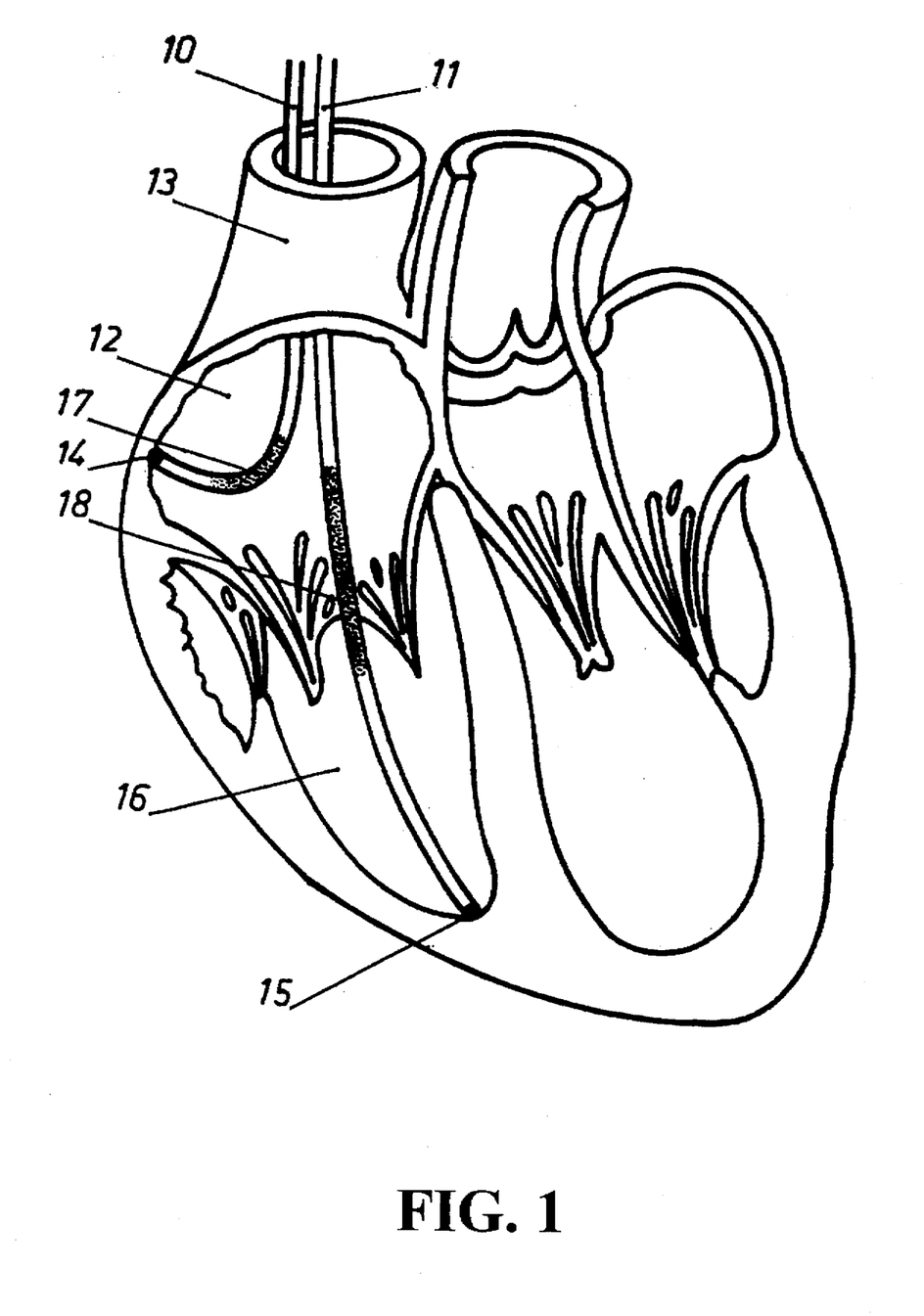
FIG. 1 is a cross-sectional four-chamber view of a human heart having implanted the atrial as well as the ventricular pacing lead.

In the embodiment of FIG. 1, there is disclosed a four-chamber cross-section of the human heart having implanted an atrial 10 as well as a ventricular 11 cardiac pacing lead. Both leads enter the right atrium 12 through the superior vena cava 13. The atrial lead is a J-shaped lead comprising an electrode 14 on its tip which is positioned in the right atrial appendage. The ventricular lead has an electrode 15 on its tip which is positioned in the right ventricle 16 in the apical position. Though unipolar leads are disclosed, bipolar leads would be also implanted in the same anatomic relation to the heart chambers. Every contraction of the heart muscle deflects both pacing leads. The atrial contraction causes the bending of the atrial lead while the ventricular contraction causes the bending of the ventricular lead. The magnitude of the lead deflection depends on the radial lead stiffness and on the heart muscle contraction forces. It also depends on the initial bending forces caused by the specific implantation position. For instance, the atrial lead implanted in the appendage will have smaller J-shape radius of the one being implanted on the anterior atrial wall. If the lead body is J-preshaped, the lead body will bear lower tension forces if implanted in the atrial appendage than if implanted on the atrial wall or septum. the lead body is straight, the lead in appendage will bear greater body tension than the lead implanted on the anterior wall or interatrial septum. Depending on the transatrial loop radius, the ventricular lead will bear some initial bending tension forces. Because of the cardiac muscle contractions, the lead body has to bear the additional dynamic lead tension forces. Every implanted lead has the part of the lead body which is mostly exposed to the bending caused by the cardiac contractions. This bending section is clearly visible on the X-ray diascopy of leads especially when a surgeon adjusts the optimal loop of the ventricular lead thus changing the magnitude of the bending deflection. The bending section 17 of the lead 10 implanted in the right atrial appendage is shaded gray, as well as it is the bending section 18 of the ventricular lead 11. Especially in chronic phase of cardiac pacing, when fibrotic tissue anchors the lead tip to the endocardium, the lead is perfectly mechanically coupled to the heart muscle. Therefore the myocardial movements forces are transferred to the lead with inconsequential losses caused by the lead elasticity which attenuates these forces. It is known from the art, that various cardiac rhythms have different hemodynamics, that means different magnitudes of contraction movements as well as different frequency spectra of these movements. For example, ventricular tachycardia impedes the cardiac contractions significantly, causing decrease of the contraction magnitude. Different cardiac rhythms cause various forces of the implanted lead mechanical tension. Furthermore, sympathetic stimulation increases the contraction acceleration being the ventricular inotropic parameter. The aim of the present invention is to enable the measurement of the implanted lead tension and thereby detect and differentiate various cardiac rhythms, as well as to achieve the closed loop regulation of rate responsive pacing.

Figure 2:
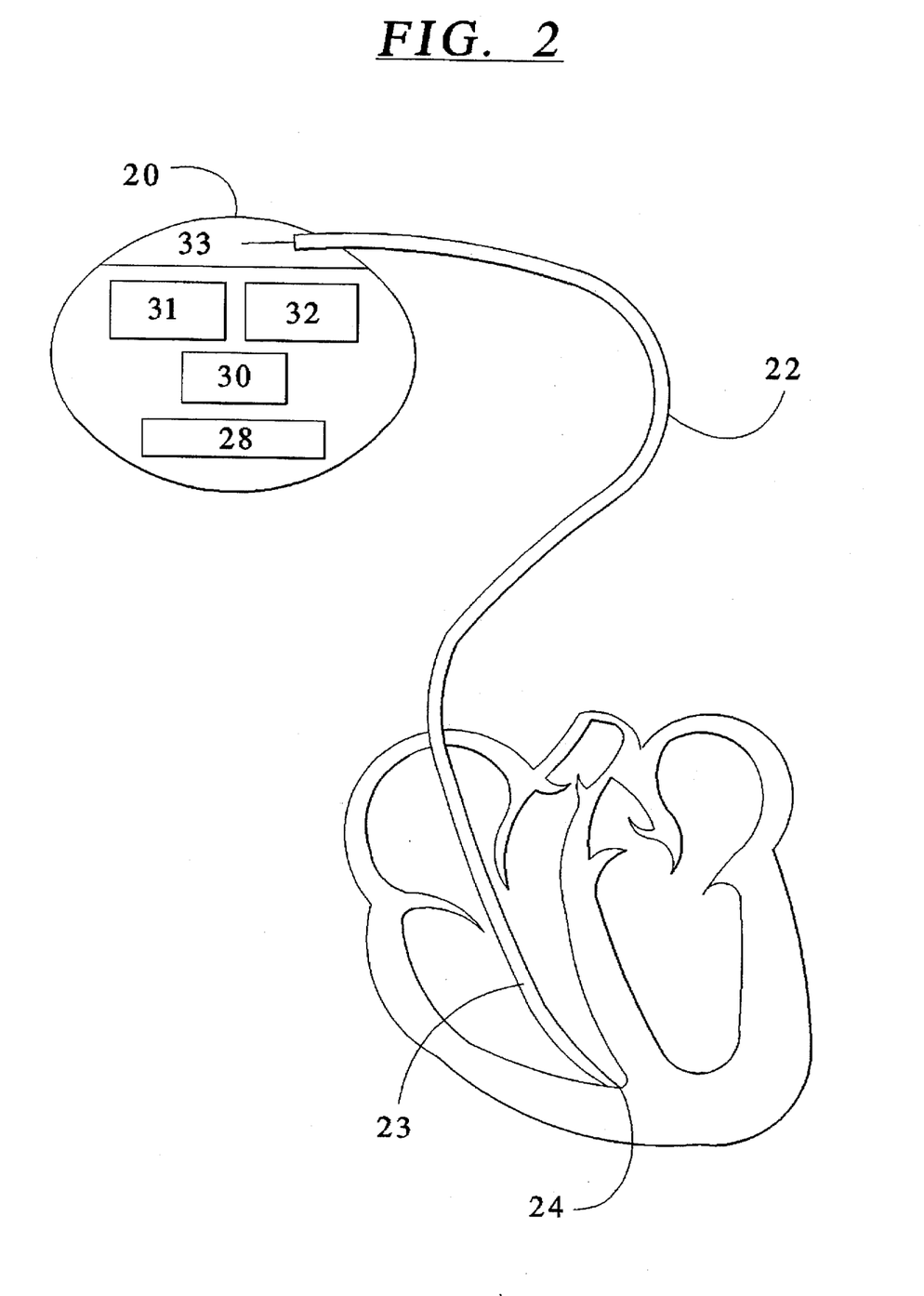
FIG. 2 is a simplified block diagram of a pacing system of this invention.

In the embodiment of FIG. 2, there is disclosed a single chamber cardiac pacing system consisting of a cardiac pacemaker 20 comprising connector assembly 33, and of a pacing lead 22, being a high frequency transmission line at least at its section 23 and being planted into the right ventricle whith its tip 24 in the apex. There are sensing—pacing circuit 32 and high frequency measurement circuit 31 within the pacemaker, which are controlled by the logic and control circuits 30 and powered by the battery 28. It is important that the lead section 23 comprising the transmission line changes its electrical parameters because of the bending within the bending section (18 in FIG. 1). The extent of a transmission line parameter change depends on the magnitude of cardiac contraction as well as the frequency spectrum of transmission line parameter variation corresponds with the frequency spectrum of the cardiac contractions.

Figure 3:
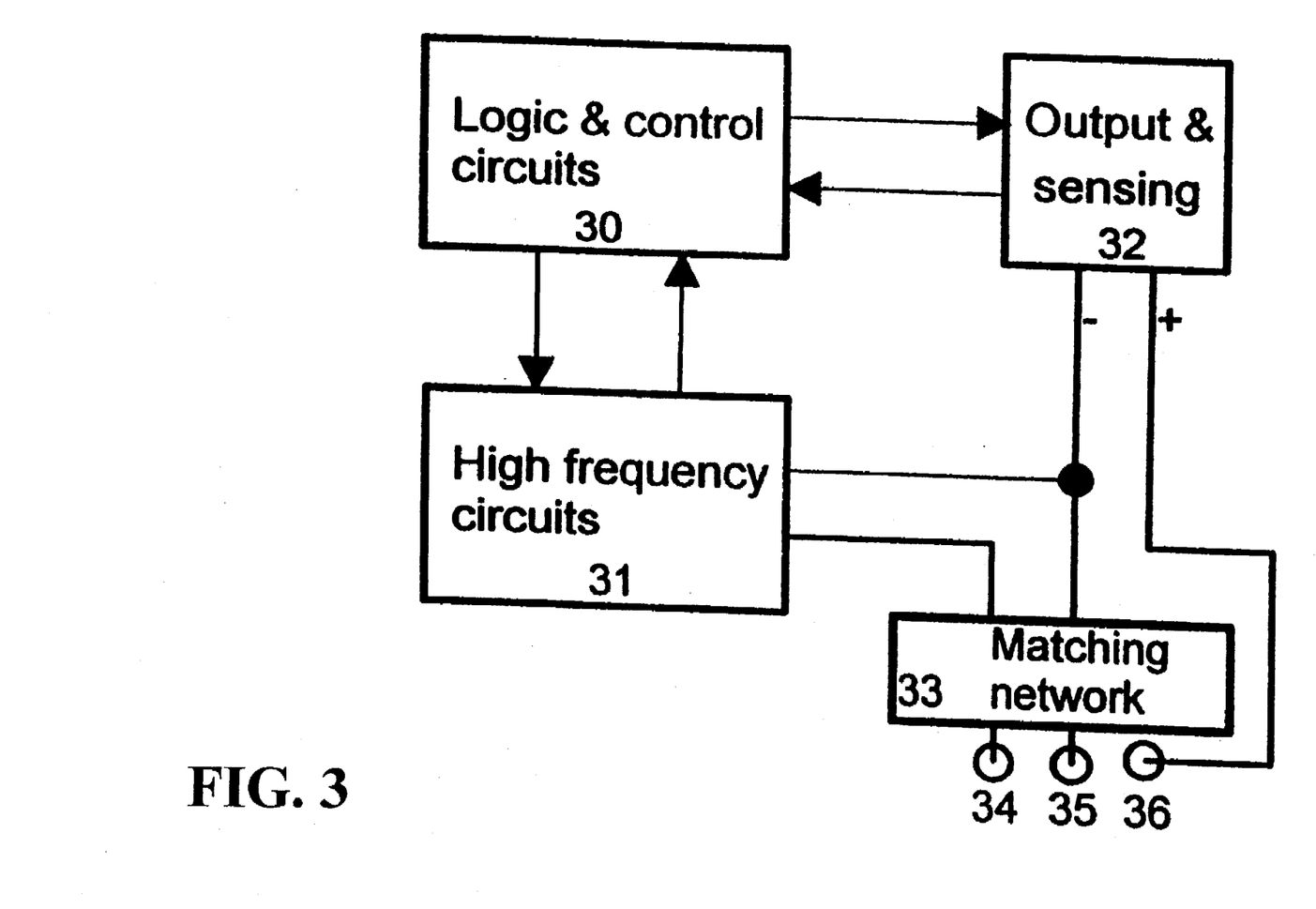
FIG. 3 is a simplified block diagram of a pacemaker of this invention.

In the embodiment of FIG. 3, there is disclosed a block diagram of the pacemaker from FIG. 2 disclosing connections among various circuits. Logic and control circuits 30 usually comprise microprocessor and memory being controlled by the software as it is disclosed in the prior art. They may also comprise telemetry and programming circuits (not shown) for radio frequency link with external programmer as it is disclosed in the prior art. Circuit 30 controls the high frequency circuit 31 as well as the output and sensing circuit 32. The circuit 31 comprises a measurement circuit which can measure and continously monitor either one of the electrical parameters of a transmission line: the input (sending end) impedance, voltage standing waves ratio VSWR and reflection coefficient. The connector assembly 33 is formed as a matching network which matches the output impedance of the high frequency circuit 31 to the characteristic impedance of the lead (not shown). Consequently, circuit 31 provides the results of measurements to the circuit 30. Circuit 32 delivers electrotherapy pulses as well as it detects the spontaneous rhythm of the patient's heart, as it is described in numerous prior art documents. Circuits of the pacemaker have to comprise three connections: two poles for the high frequency signal and two poles for the pacing-sensing signal. Accordingly, connections 34 and 35 are used to connect the high frequency circuit 31 and connections 35 and 36 are used to connect the pacing-sensing circuit 32. In unipolar pacing system, connections 34 and 35 are pins of the connector assembly, while connection 36 is a pacemaker case. Consequently, pin 35 is used for pacing lead conductor connection, while pins 34 and 35 are used to connect the transmission line. In bipolar pacing system, connections 34, 35 and 36 are pins of the connector assembly. Consequently, pins 35 and 36 are used for two pacing lead conductors connection, while pins 34 and 35 are used to connect the transmission line. In both systems, pin 35 is connected to the active pacing electrode of a lead, while pin 36 is connected to the indifferent electrode.

Figure 4:
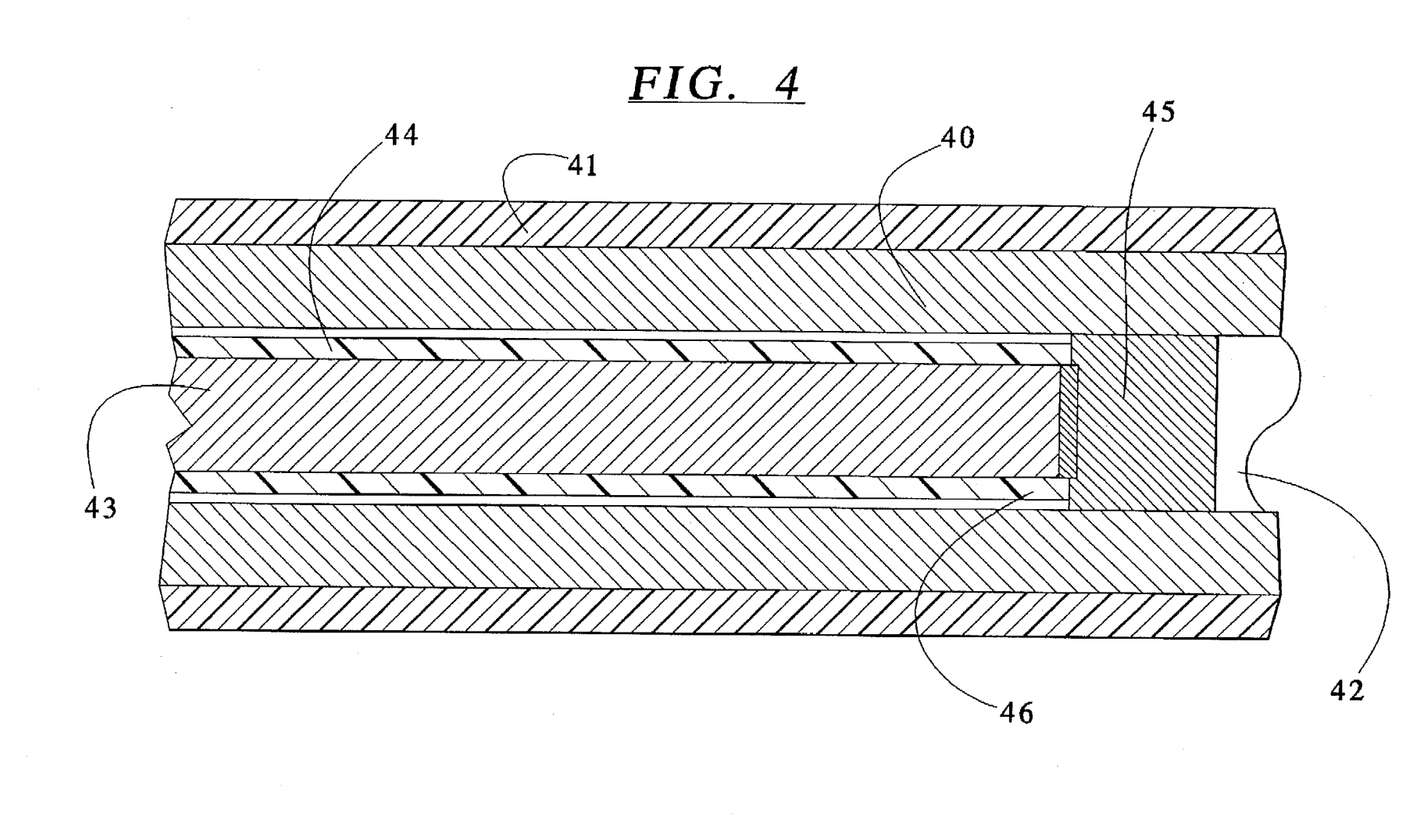
FIG. 4 is a cross-section of a lead section comprising stylet, being the transmission line.

In the embodiment of FIG. 4, there is disclosed one example of tensiometric transmission line designed as a lead stylet. Actually, the section of an unipolar lead, being the receiving end of the transmission line, is disclosed having lead conductor 40 and insulation sheath 41. There is only one lead conductor in unipolar lead having a styler channel 42. Precise design of lead conductor 40 is not shown because it is not important for understanding of physical and electric principle of this invention however, as it is known from the prior art, it may be helically wounded wire or multifiliar strip, or any other different design. Despite the conductor 40 design, the electrical principle remains the same. The conductive stylet wire 43, insulated by an insulation sheath 44 is inserted within the channel 42. On the distal end of the stylet 43, there is a termination 45, being electrically connected to the styler wire 43 by means of the joint 46 formed either by solder or by conductive glue.

In the example of this embodiment, the termination 45 is disclosed to be a cylinder. The termination 45 maintains the sliding electrical contact with the lead conductor 40. Lead conductor 40, insulation 44 and wire 43 constitute a coaxial cable insulated by insulation 41. At high frequency, this is a transmission line has a characteristic impedance. The proximal end of the lead, being the sending end of the tensiometric transmission line, is not shown. However, as it is disclosed in prior art documents, every lead comprises the appropriate connector to the pacemaker. In this particular embodiment, such a connector would ensure the electrical connection between lead conductor 40 and pin 35, as well as between stylet wire 43 and pin 34. This connector may not affect the impedance matching between the transmission line and the pacemaker high frequency circuits. Termination 45 may be designed to be either an open circuit or a short circuit between conductor 40 and wire 43. Termination 45 may be also an impedance matched to the characteristic line impedance. Normally, the lead tension causes thepressure onto the styler insulation 44. If the lead section is exposed to bending, the insulation sheet 44 will be distended and compressed rhythmically corresponding to the heart beats.

Accordingly, the geometry of coaxial cable will change. Consequently, the characteristic line impedance will also change. Therefore the insulation sheet 44 has to be made of a soft material susceptible to compression and distension. For instance, if the transmission line is terminated by a matched impedance, there will be no reflections, and the measured VSWR is approximately equal to unity. The input line impedance is than equal to the characteristic line impedance. Geometry variation of the transmission line causes variation of the characteristic line impedance.

Accordingly, variation of matching at the sending end as well as at the receiving end occurs. Therefore, variation of either VSWR, or reflection coefficient, or input impedance can be measured at the sending end (pacemaker high frequency circuits) of transmission line.

Figure 5:
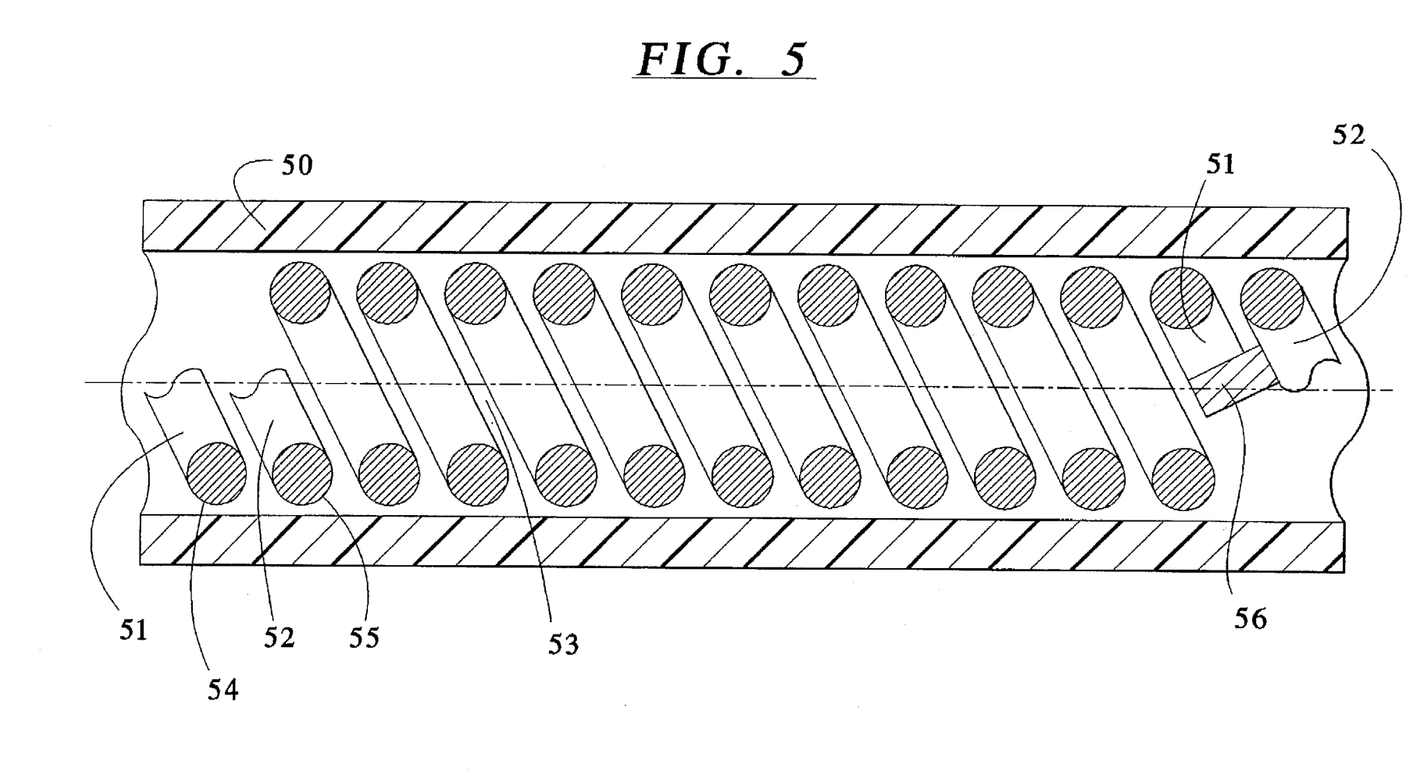
FIG. 5 is a cross-section of a lead section designed to be a transmission line.

In the embodiment of FIG. 5 there is disclosed a cross-section of the unipolar lead section designed to be a special kind of transmission line. The lead comprises an insulation tube 50, and two helically wound lead conductors 51 and 52. Conductor 51 and conductor 52 are wounded one adjacent to the another in such a way as to constitute a stylet channel 53. Insulation tube 50 is usually made of either silicone or polyurethane. Conductors 51 and 52 are insulated by thin insulation coatings 54 and 55, respectively. If the lead were implanted within the human body, body fluid penetrates after some time through the insulation tube 50. Accordingly, bending of the lead body 50 causes the variation of the conductance between the two conductors 51 and 52 due to the local variation of mutual distance between conductors. Even more influential is the change of inductance caused by the variation of distance between the two conductors. The proximal end of the lead, being the sending end of the tensiometric transmission line, is not shown. However, as it is disclosed in prior art documents, it comprises the appropriate connector to the pacemaker. In this particular embodiment, such a connector would ensure the electrical connection between lead conductor 51 and pin 34, as well as between lead conductor 52 and pin 35. This connector may not affect the impedance matching between the transmission line and the pacemaker high frequency circuits. The receiving end of the transmission line comprises a termination 56 being electrically connected to both lead conductors 51 and 52. Due to the lead body bending, the geometry of the lead changes rhythmically corresponding to the mechanical contractions. Consequently, the transmission line parameters deviate rhythmically as well as synchronously with cardiac contractions. Distal part of the lead is not shown, but it is terminated by an electrode having electrical contact with the lead conductor 52. In the embodiment of this example, lead conductor 52 is used for pacing-sensing signal transmission, while both lead conductors 51 and 52 constitute the transmission line.

Figure 6:
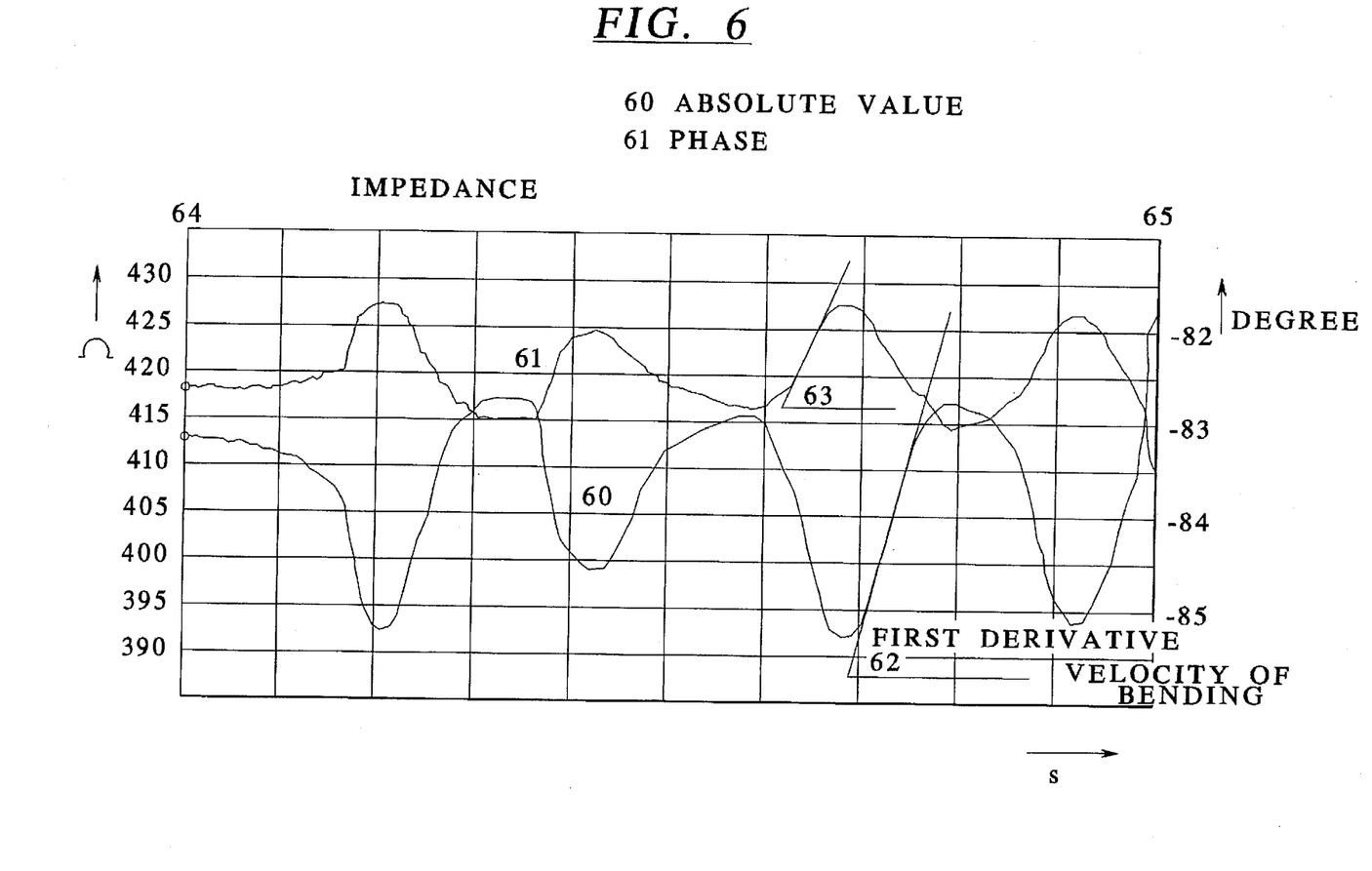
FIG. 6 is an example of high frequency measurement on the open circuited pacing lead comprising the transmission line which was rhythmically bent.

In FIG. 6, there is disclosed a diagram showing the result of measurement of the sending end vector impedance of the lead such as disclosed in FIG. 5. Lead conductors were teflone insulated helicoidally wounded multistrand wires. The line termination 56 was the open circuit. The coaxial connector of the lead was connected to the high accuracy network analyzer measurement instrument. The section of the lead, such as disclosed in FIG. 5, was tied between closure of left thumb and left index finger and closure of right thumb and right index finger. The lead was intentionally bent in the section between the two hands by means of the rhythmic motion of the two hands. FIG. 6 discloses sending end vector impedance: its absolute value 60 and phase 61 as functions of time. The frequency of the input signal was 20 MHz. As it is demonstrated, lead bending causes variation of sending end vector impedance. Moreover, the first derivative of the impedance 62 as well of the phase 63 is proportional to the velocity of bending. The left numbers column 64 designates the values of the absolute value in Ohms. The right numbers column 65 designates the values of the phase in degrees. The lead implanted within the human heart will therefore provide signal representing the cardiac contraction. Every pacing pulse must be followed by the cardiac contraction i.e. transmission line parameters variation. Different cardiac arrhythmias produce different patterns of transmission line parameters variation. The first derivative of the transmission line parameter variation is the ventricular inotropic parameter used for closed loop pacing rate regulation. Accordingly, this invention enables pacing capture confirmation, tachycardia detection and rate responsive pacing.

Figure 7:
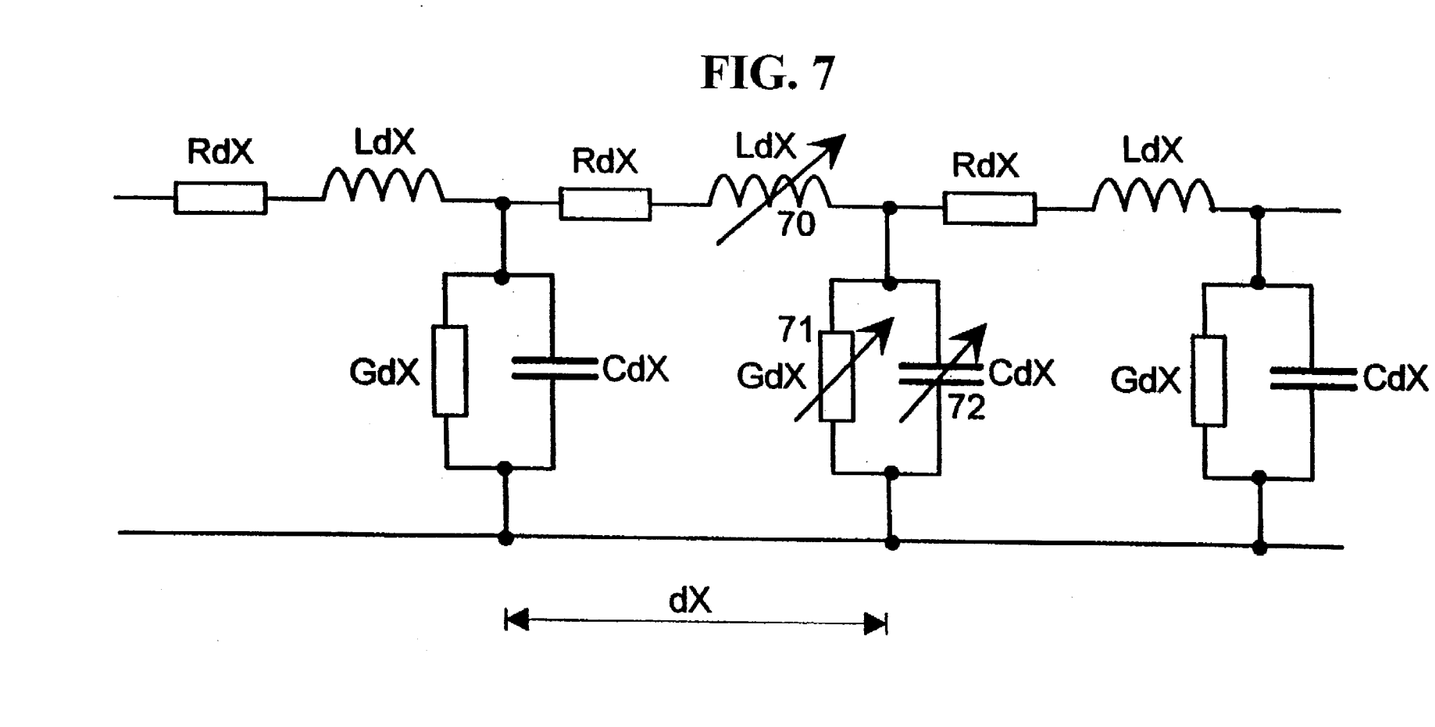
FIG. 7 is an example of the equivalent circuit of the lead section.

FIG. 7 shows the equivalent circuit of a pacing lead section being the transmission line 3dx long. This Fig. explains the theoretical background of this invention. Designation L is for distributed inductance per unit length representing the effect of the variation of magnetic flux set up around the conductors. Designation C is for distributed capacitance (per unit length) between the conductors. Distributed resistance per unit length R represents the imperfection of the conductors. Distributed conductance per unit length G represents the imperfection of the insulation. These designations are common in the transmission lines theory. Lead bending causes the variation of capacitance Cdx, conductance Gdx and inductance Ldx, at the location of lead geometry variation. Accordingly, variable inductance 70, variable conductance 71 and variable capacitance 72 are disclosed. However, in various examples of possible lead designs, there will be different power of the variation of these three parameters varying the line impedance. The dry lead from FIG. 4 will mainly change the capacitance Cdx. After a certain post-implant period, body fluid will soak the insulation and the conductance Gdx variation becomes more influential.

The lead from FIG. 5 will mainly change the inductance Ldx, but the influence of capacitance and conductance is not negligible. Accordingly, lead may be designed in such a way as to achieve the sensitivity of either three line parameters on the lead bending i.e. geometry variation. There is also another possible embodiment of disclosed system, being almost the same and having same electrical connections, wherein transmission line maintains its geometry and its parameters constant despite of the lead body tension, but has a termination on its distal end which is susceptible to lead body tension. Accordingly, the impedance of the termination varies dependent on heart muscle contractions, causing the mismatching between the line impedance and the termination impedance.

These principles are not limited to the leads. A transmission line, susceptible to change of its parameters because of geometry variation, may also be incorporated within the implantable defibrillator patch.

In the embodiment of FIG. 8, there is disclosed a cross-section of a defibrillator patch. The patch is made of the elastic insulation material 80, usually silicon rubber. The conductive surface 81 is defibrillating electrode, usually made of wire mesh. A lead conductor 82 is electrically coupled to the electrode 81 by means of a junction 83 and electrically connects the electrode 81 to the electrotherapy output circuit of an implantable defibrillator (not shown). A second lead conductor 84 is electrically connected to the second conductive wire mesh 86 by means of a junction 85. Conductive gluing or even point welding may be used for junctions 83 and 85. There is an elastic insulation layer 87 between electrode 81 and conductive mesh 86. Defibrillating electrode 81, insulation layer 87 and mesh 86 are mounted in parallel planes having the equivalent surface and create a capacitor. Both lead conductors 82 and 84 are built in a coaxial bipolar lead wire, insulated by silicone 88 as it is known in the art, and create a coaxial cable being the transmission line. In disclosed embodiment, the coaxial transmission line is terminated by a capacitor. Bending of the patch deforms the wire meshes 81 and 86 as well as it distends and compresses the insulation layer 87. Accordingly, the capacitance of the capacitor 81-87-86 is modulated by the cardiac contractions. Therefore, if the sending end transmission line parameters of the coaxial lead conductor 82-88-84 are measured at the proximal end (not shown) of the lead conductor, the measured parameters are modulated by the cardiac contractions.

There have been described two major principles of the invention:

1. The transmission line is sensitive to the bending, and the transmission line parameters are modulated by the cardiac contractions; the transmission line must be implanted within the bending segment of the lead (FIG. 4 and 5).

2. The transmission line is not sensitive to the bending, and the transmission line is terminated by the load which forms the sensor portion and wherein the load parameters are modulated by the cardiac contractions; termination of the transmission line comprising the load must be implanted within the bending segment of the lead (FIG. 8).

While specific embodiments of present invention have been described, it should be understood that these embodiments are described for purposes of illustration only. The foregoing description is not intended in any way to limit the scope of the present invention. Rather is the intention that the scope of the invention be limited only as defined in the appended claims.

I claim:

1. An implantable electromedical device comprising:
   an elongated elastic lead body having a first electrical conductor contained within said lead body and terminating at a first end in an electrode connectable in vivo to a heart;
   said lead body including a sensor portion disposed at a location for undergoing deformations responsive to heart muscle contractions when said lead body is connected to said heart;
   said lead body comprising high frequency transmission line means, including said first electrical conductor and a second electrical conductor with respective terminals at a second end of said lead body opposite said first end, for transmitting, via said first and second electrical conductors, high frequency signals from said terminals to said sensor portion of said lead body and vice versa;
   electronic circuitry means connectable to said terminals at said proximal end of said transmission line means for transmitting high frequency signals in a range from about 5 MHZ to about 100 MHZ to said transmission line means;
   said sensor portion reflecting said high frequency signals and having an electrical parameter which varies when said sensor portion is subjected to said deformations, the varying of said electrical parameter causing a reflected high frequency signal from said sensor portion to be modified relative the high frequency signal from said electronic circuitry means; and
   said electronic circuitry means further comprising means for analyzing said reflected high frequency signal for identifying at least one characteristic of said heart muscle contractions.

2. A device as claimed in claim 1 wherein said sensor portion comprises at least a part of said first and second electrical conductors.

3. A device as claimed in claim 1 wherein said sensor portion comprises means for terminating said transmission line means electrically connected at said first end of said first and second electrical conductors.

4. A device as claimed in claim 1 wherein said electrical parameter comprises an impedance of said transmission line means at said second end of said lead body.

5. A device as claimed in claim 1 wherein said electrical parameter comprises a reflection coefficient of said transmission line means.

6. A device as claimed in claim 1 wherein said electrical parameter comprises a voltage standing wave ratio of said transmission line means.

7. A device as claimed in claim 1 further comprising two electrically conductive elements respectively connected to said first and second electrical conductors, and wherein said electrical parameter comprises a capacitance between said two electrically conductive elements.

8. A device as claimed in claim 1 wherein said electrical parameter comprises a capacitance between said first and second electrical conductors.

9. A device as claimed in claim 1 wherein said electronic circuitry means comprise means for matching an output impedance of said electronic circuity means to an input impedance of said transmission line means.

10. A device as claimed in claim 1 wherein said electronic circuitry means further comprise cardiac pacing means for emitting pacing pulses for delivery to said heart via said first electrical conductor at said electrode, and control means responsive to said at least one characteristic of said heart muscle contractions for controlling said pacing signals.

11. A device as claimed in claim 10 wherein said first electrical conductor has an interior stylet channel, and wherein said second electrical conductor comprises an insulated stylet wire disposed in said styler channel at a location at which deformation of said lead body occurs when said lead body is connected to said heart, said insulated stylet wire and said first electrical conductor forming said transmission line means, and said transmission line means varying said electrical parameter of said sensor region dependent on a frequency and magnitude of said heart muscle contractions.

12. A device as claimed in claim 11 wherein said electrical circuitry means has first and second poles, and wherein said first electrical conductor is connected to said first pole and said stylet wire is connected to said second pole.

13. A device as claimed in claim 10 wherein said second electrical conductor comprises an electrical conductor contained within said lead body together with said first electrical conductor and terminating at said distal electrode, said second electrical conductor and said first electrical conductor forming said transmission line means, which varies said electrical parameter of said sensor portion dependent on a frequency and magnitude of said heart muscle contractions.

14. A device as claimed in claim 13 wherein said electrical circuitry means has first and second poles, and wherein said first electrical conductor is connected to said first pole and said second electrical conductor is connected to said second pole.

15. A device as claimed in claim 10 wherein said electronic circuitry means comprises means for generating a measurement signal representing varying of said electrical parameter caused by variation of the geometry of said transmission line means, said measurement signal being generated by said heart muscle contractions and said measurement signal having amplitude and frequency characteristics representing amplitude and frequency characteristics of said heart muscle contractions.

16. A device as claimed in claim 15 wherein said electronic circuitry means comprise a high frequency bridge, said high frequency bridge being balanced when no force is applied to said sensor portion and said high frequency bridge being unbalanced whenever a force is applied to said sensor portion.

17. A device as claimed in claim 15 wherein said sensor portion has an initial force thereon, and wherein said electronic circuitry means comprise a high frequency bridge, said high frequency bridge being balanced when only said initial force is applied to said sensor portion, and said high frequency bridge being unbalanced whenever a force other than said initial force is applied to said sensor portion.

18. A device as claimed in claim 10 wherein said control means include means for detecting cardiac arrhythmia and for differentiating among various arrhythmias.

19. A device as claimed in claim 10 wherein said control means include means for modulating a pacing rate in a rate responsive pacing mode.

20. A device as claimed in claim 10 wherein said control means include means for confirming pacing capture.

21. A device as claimed in claim 10 wherein said first electrical conductor has a connector at said second end of said lead body, said connector making an electrical connection between said transmission line means and said electronic circuitry means without affecting impedance matching between said transmission line means and said electronic circuitry means.

22. A device as claimed in claim 1 wherein said transmission line means comprises means for terminating said transmission line means disposed at said first end of said lead body.

23. A device as claimed in claim 22 wherein said means for terminating comprise an open circuit.

24. A device as claimed in claim 22 wherein said means for terminating comprise a short circuit.

25. A device as claimed in claim 22 wherein said means for terminating have an impedance matched to an impedance of said transmission line means.

26. A device as claimed in claim 22 wherein said means for terminating has a variable impedance and comprises means for varying said variable impedance dependent on lead body tension caused by said heart muscle contractions, said impedance variation generating mismatching of said means for terminating to said transmission line means, said mismatching having a frequency and a magnitude dependent on a frequency and magnitude of said heart muscle contractions.

* * * * *